US006482584B1

(12) United States Patent
Mills et al.

(10) Patent No.: US 6,482,584 B1
(45) Date of Patent: Nov. 19, 2002

(54) CYCLIC IMPLANT PERFUSION CLEANING AND PASSIVATION PROCESS

(75) Inventors: C. Randal Mills, Alachua; John F. Wironen, Gainesville, both of FL (US)

(73) Assignee: Regeneration Technologies, Inc., Alachua, FL (US)

( * ) Notice: Subject to any disclaimer, the term of this patent is extended or adjusted under 35 U.S.C. 154(b) by 0 days.

(21) Appl. No.: 09/191,232

(22) Filed: Nov. 13, 1998

(51) Int. Cl.$^7$ ................................................. A01N 1/02
(52) U.S. Cl. ............................ 435/1.1; 435/1.2; 422/33
(58) Field of Search ..................... 435/1.1, 1.2; 600/36; 623/16; 422/33

(56) References Cited

U.S. PATENT DOCUMENTS

| | | |
|---|---|---|
| 3,291,640 A | 12/1966 | Livingston |
| 4,193,818 A | 3/1980 | Young et al. |
| 4,294,753 A | 10/1981 | Urist |
| 5,288,462 A | 2/1994 | Carter et al. |
| 5,298,222 A | 3/1994 | O'Leary |
| 5,333,626 A | 8/1994 | Morse et al. |
| 5,380,826 A | 1/1995 | Castor et al. |
| 5,429,810 A | 7/1995 | Knaepler et al. |
| 5,509,968 A | 4/1996 | Carr |
| 5,513,662 A | 5/1996 | Morse et al. |
| 5,556,379 A | 9/1996 | Wolfinbarger |
| 5,716,454 A | 2/1998 | Carr |
| 5,725,579 A | 3/1998 | Fages et al. |
| 5,797,871 A | 8/1998 | Wolfinbarger, Jr. |
| 5,846,484 A | 12/1998 | Scarborough et al. |
| 5,993,844 A | 11/1999 | Abraham et al. |
| 6,024,735 A | 2/2000 | Wolfinbarger, Jr. |
| 6,102,056 A | 8/2000 | Kotsopey |

FOREIGN PATENT DOCUMENTS

| | | |
|---|---|---|
| EP | 0424159 A2 | 10/1990 |
| JP | 03/224570 | 1/1990 |
| WO | WO 94/11035 | 5/1994 |
| WO | WO 97/27882 | 7/1997 |
| WO | WO98/41245 | 9/1998 |

OTHER PUBLICATIONS

Carr, James, et al. "A Feasability Study for Removing Tissue Contamination from Porous Implants." Biomedical Instrumentation and Technology. May/Jun. 1995. 220–225.
Levine, David, et al. "Cost Awareness and Containment for the 1990's: Recycling Orthopaedic Implants." Contemporary Orthopaedics, Oct. 1992. 25(4):376–381.
American National Standard. "Good Hospital Practice: Handling and Biological Decontamination of Reusable Medical Devices." Association for the Advancement of Medical Instrumentation, 1991. 1–14.
Brown, John Stuart. "An Ultrasonic Cleaning Bath in General Practice." Practioner, Apr. 8, 1988. 232:377.
University of Florida Tissue Bank, Inc. "Threaded Cotical Dowel: Processing and Screening Methods." Technical Monograph, 1996. 1–6.
Grafton Deminineralized Bone Matrix (DBM) "First Consider the Source: Musculoskeletal Transplant Foundation." Osteotech, Inc., 1995.
Wolfinbarger, et al. "A Comprehensive Study of Physical Parameters, Biomechanical Properties, and Statistical Correlations of Iliac Crest Bone Wedges Used in Spinal Fusion Surgery." Spine, 1994. 19(3):277–283.
Stanford, C.M. et al. "Bone Cell Expression on Titanium Surfaces is Altered by Sterilization Treatments." J Dent Res, May 1994. 73(5):1061–1071.
Evanoff, Jean. "Sterilizing and Preserving Human Bone." AORN Journal, Apr. 1983. 37(5):972–980.
Petri, W.H., et al. "Demineralized Bone Sterilization." J Dent Res, 1993. 72 (IADR Abstracts) 417, #2511.
Bloom, D.S., et al. "Effect of Multiple Sterilization in the Monocortical Screw–Bone Interface." J Dent Res, 1996. 75 (IADR Abstracts) 335 # 2537.
Liu, Yu et al. "Detergent Treatment on Canine Tracheal Allograft." Transplantation, 1999. 67(9):S649, #425.
Voggenreiter, G. et al. "Effects of Preservation and Sterilization on the Biomechanical Properties of Cortical Bone Grafts." J. Biomechanics, 1991. 24(6):458.
Mschvidobadse, Von M.V. "Allogenic Transplantation of Sterilized Bones and Halfjoints." Zbl. Chirurgie, 1978. 103: 1138–1148, Abstract Only In English—No Translation.
American Red Cross, "Aseptically–Processes Bone and Connective Tissue." ARC, North Central Region, 1995.

(List continued on next page.)

Primary Examiner—Sandra E. Saucier
(74) Attorney, Agent, or Firm—Van Dyke & Associates, P.A.

(57) ABSTRACT

This invention is a novel method for perfusion of a porous implant which achieves efficient interpenetration of desired factors into and removal of undesirable factors from the pores of the implant, cleaning of the implant, efficient passivation of the implant (inactivation of pathogens, microorganisms, cells, viruses and the like and reduction in antigenicity thereof), and the novel implant produced by such treatment. The process presents a system wherein the rate of pressure cycling, the fact of pressure cycling, and the amplitude of pressure cycling, results in highly cleaned tissues and other implants for implantation. Target decontamination goals for this process include between about a one (1) to twelve (12) log reduction in bacterial contamination, between about a one (1) to fifteen (15) log reduction in enveloped virus contamination, up to about a five (5) log reduction in non-enveloped virus contamination, between about a two (2) to ten (10) fold reduction in endotoxin, maintenance of implant or graft biologic and biomechanical properties, absence of tissue toxicity due to cleaning solutions used, and reduced implant antigenicity.

32 Claims, 13 Drawing Sheets

(6 of 13 Drawing Sheet(s) Filed in Color)

OTHER PUBLICATIONS

Database WPI, Section PQ, Week 199429, Dewetn Publications, Ltd., London, GB; Class P32, AN 1994–239698, XP002135434 & SU 1 811 817 A (Traumatology Orthopaedy Res Inst.), Apr. 30, 1993 abstract.

Maddox, Ewa, et al. "Optimizing Human Demineralized Bone Matrix for Clinical Application" Burgess, 529–534.

Piet, M.P.J., et al., The use of tri(n–butyl) phosphate detergent mixtures to inactivate hepatitis viruses and human immunodeficiency virus in plasma and plasma's subsequent fractionation, Transfusion vol. 30, No.: 7, 1990, pp. 591–598.

Hellstern, et al., Vox Sang, 1992:63:178–185, Manufacture and in vitro Characterization of Solvent/Detergent–Treated Human Plasma.

Horowitz, B. et al., Solvent/Detergent–Treated Plasma: A Virus–Inactivated Substitute for Fresh Frozen Plasma, Blood 79:826–831 (1992).

CYCLIC IMPLANT PERFUSION CLEANING AND PASSIVATION PROCESS

BACKGROUND OF THE INVENTION

1. Field of the Invention

This invention is a novel method for perfusion of a porous implant which achieves efficient interpenetration of desired factors into the pores or channels of the implant, cleaning of the implant, efficient passivation of the implant (inactivation of pathogens, microorganisms, cells, viruses and the like and reduction in antigenicity thereof), and the novel implant produced by such treatment.

2. Description of Known Procedures For Implant Treatment

As used in this disclosure, the term "implant" refers to any material the implantation of which into a human or an animal is considered to be beneficial. Accordingly, the implant may be tissue-derived material, such as bone, skin, and the like, or it may be a metallic or synthetic material having an internal structure that may require cleaning or sterilization. Bearing this definition in mind, it will be apparent that many procedures have been described in the art for treatment of implants to either clean such implant, inactivate contaminating microorganisms or cells that may be present in or on such implant, or to infuse the implant with desirable factors. This section of the disclosure discusses several known methods for achieving one or more of these results, in order to more clearly and definitively set forth that which has been invented, and which is disclosed and claimed as novel and inventive, as defined by the claims appended hereto.

European Patent Application No. EP 0 424 159 (Osteotech)—"Aseptic Processing of Allograft Bone and Tissue," (published Apr. 24, 1991, based on a U.S. Priority application filed Oct. 9, 1989), is an extremely general disclosure relating to aseptic processing of allograft bone and issue. It appears that the intent of this application was to establish an early priority date in an effort to foreclose the entire field of aseptic processing of allograft bone and tissue. However, he disclosure is so general that it does not appear to contain an enabling disclosure of any protectible allograft sterilization method. No U.S. or European patent related to this extremely general published application appears to have ever issued.

In U.S. Pat. No. 5,333,626 (Cryolife)—"Preparation of Bone for Transplantation", (issued on Aug. 2, 1994, based on an application filed on Dec. 31, 1991), relates to a method of preparing bone for transplantation by maintaining the internal matrix of the bone to be implanted, preferably at high pressure, in the presence of a decontaminating agent, preferably polyvinyl pyrrolidine-iodine (PVP-I) optionally in the presence of a detergent, in solution. The "high pressure" feature of this patent is described at column 5, lines 10—31: "High pressure washing conditions should provide a force sufficient to drive the cleaning solution into internal matrix of the bone. Such high pressure washing conditions include, for example, vigorous agitation, such as with a paint can shaker, or high pressure lavage such as with a high pressure liquid jet stream . . . The pressure of the liquid jet stream is preferably 100 to 3,000 psi and most preferably 500 to 1,500 psi." However, the patent does not disclose or suggest exposure of an implant to an oscillating atmospheric pressure, the referenced patent requires pressures significantly higher than those required according to the present invention, and it is only applicable to bone, while the present invention is applicable to bone or soft tissue. In addition, the claimed process requires approximately 1–2 days to complete.

In U.S. Pat. No. 5,513,662 (Osteotech)—"Preparation of Bone for Transplantation" (this patent issued on May 7, 1996 as a continuation-in-part of the application that issued as the U.S. Pat. No. 5,333,626 patent, based on an application filed on Jan. 21, 1994, and claiming priority to the Dec. 31, 1991 filing date of the application on which the U.S. Pat. No. 5,333,626 patent is based), relates to a method of preparing bone for transplantation in which the internal matrix of the bone is maintained at a pressure below one atmosphere. It is disclosed (column 10, lines 13–19) that "optimum times for maintaining pressure below ambient are generally in the range of 30 to 60 minutes but can be determined for each application by monitoring progress of blood and lipid extraction (see Example 10)." It is further disclosed that generally use of gas pressure below ambient for less than two minutes will be ineffective and use for longer than five hours will confer no further benefit. Thus, the '662 patent requires that the bone be maintained for substantial periods of time at pressures below one atmosphere. There is no disclosure or suggestion of rapidly cycling between elevated and decreased pressures, even though it is suggested that the bone might first be treated at an elevated pressure, followed by a treatment step at a pressure below atmospheric pressure (see, for example, claim 3, column 15). The present invention discloses a process wherein transient and cyclical exposure of an implant material to a given pressure achieves the desired result of implant cleaning, perfusion or passivation.

In U.S. Pat. No. 5,556,379 (LifeNet Research Foundation)—"Process for Cleaning Large Bone Grafts and Bone Grafts Produced Thereby," (issued on Sep. 17, 1996 based on an application filed on Feb. 27, 1995, and claiming priority of an earlier, abandoned application, filed Aug. 19, 1994), describes the "Allowash™" process. The patent is explicitly directed to the removal of "bone marrow from the luminal and cancellous bone spaces in large, essentially whole, bone grafts." (See Summary of the Invention). Accordingly, the referenced patent is directed only to treatment of bone, which has to be largely intact. The stated intent in applying the process to essentially whole bone grafts is to reduce the load of potentially virus carrying bone marrow to facilitate preparation of smaller bone grafts therefrom. The process involves applying a vacuum to the bone graft to draw solution capable of solubilizing bone marrow through articulating cartilaginous surfaces and through the intact bone's intramedullary canal or other bone cavity. The patent neither discloses nor suggests a method in which oscillating pressures are used to clean a bone graft.

U.S. Pat. No. 5,380,826 (Aphios Corporation)—"Supercritical Fluid Disruption of and Extraction from Microbial Cells, (issued on Jan. 10, 1995, based on an application filed on Sep. 29, 1992), relates to a method for harvesting intracellular components by exposing cells to an elevated pressure in the presence of a solvent, and then rapidly and suddenly releasing the pressure to effect disruption of the cells. The patent also discloses an apparatus for carrying out this process continuously. However, this patent neither discloses nor suggests applying the cell disruption method to allograft bone.

U.S. Pat. No. 5,288,462 (Stephen D. Carter)—"Sterilization Apparatus and Method" (issued on Feb. 22, 1994, based on an application filed on May 18, 1992), describes a chamber for receiving a material to be sterilized by repeatedly subjecting the chamber to elevated pressures, followed by sudden release of the pressure, i.e. "explosive decompression." The patent requires that the chamber be pressurized to at least 1000 psi. The patent neither discloses, suggests, nor claims application of this method or chamber to sterilization of bone materials. There is no disclosure of cleaning solutions used in connection with the described apparatus that would be effective in sterilizing the matrix of a bone. There is no disclosure that would allow one skilled in the art to determine, without undue experimentation, that bone could be sterilized in this apparatus. In addition, there is no disclosure nor suggestion that an implant could be sterilized without use of such highly elevated pressures, but merely by oscillation of lower absolute pressures.

U.S. Pat. No. 5,725,579 (Bioland)—"Process for Treating Bone Tissue and corresponding Implantable Biomaterials", (issued Mar. 10, 1998, based on a priority French application filed Dec. 21, 1992 and an earlier U.S. priority filing of Dec. 9, 1993), is directed to a method of cleaning bone by exposing the bone to a supercritical fluid. As best as can be understood from this patent, this involves exposing bone to carbon dioxide at elevated pressures, in order to solubilize lipids.

Tissue sterilization methods known in the art have undesirable attributes. Gamma irradiation, in order to ensure destruction of pathogens, such as the human immunodeficiency virus (HIV), has to be used at doses that result in tissue destruction (e.g. 3.5 Mrad; see, for example, Rasmussen, et al., J. Arthroscopic and Related Surgery, 10(2):188–197, (1994); Goertzen, et al., British Soc. of Bone and Joint Surg., 77:204–211 (1005); Loty, et al., International Orthopaedics, 14:237–242, (1990)). Use of ethylene oxide has been found to result in implants that produce inflammatory responses (Kudryk, et al., J. Biomedical Materials, 26:1477–1488, (1992); Thoren, et al., Clin. Orthopaedics, 318:259–263, (1995); Simonian, et al., Clin. Orthopaedics, 302:290–296, (1994); Jackson, et al., Am. J. Sports Medicine, 18:1–9, (1990)). Standard chemical solution treatments, while effective in sterilizing surfaces with which the solutions are brought into contact, have the major disadvantage of being insufficiently penetrating to reach the interstices of tissues, where potentially pathogenic organisms may reside. In view of these shortcomings, there remains a long-felt-need for an optimized tissue sterilization process, which would incorporate some or all of the following features: Effective removal or inactivation of a wide range of bacterial and viral pathogens; absence of graft toxicity; retention of desirable tissue characteristics, such as biomechanical strength or growth-inducing properties; effectiveness across a wide range of operating modifications and for a wide variety of tissue types; ability to conclude the process in a final implant tissue container, to ensure sterile packaging and delivery for implantation.

In view of the foregoing review of the known art relating to implant treatment and sterilization methods, it is believed that the present invention provides a long needed improvement in that no absolute temperatures or pressures are required to achieve efficient implant cleaning, perfusion, or passivation. In addition, the instant method does not require drilling of holes in implant materials or any other manipulation or modification in order to achieve efficient implant cleaning and sterilization. Furthermore, the present method permits safe pooling of donor tissue for implant production at economies of scale, without at the same time diminishing the desirable biological properties of the pooled implant materials. The instant process includes a number of methodologies, the additive effect of which is the production of highly cleansed, sterilized (passivated) tissues, which may be implanted, without causing toxicity to the recipient. Various embodiments of the method of this invention includes all of the above listed features, namely: effective removal or inactivation of a wide range of bacterial and viral pathogens; absence of graft toxicity; retention of desirable tissue characteristics, such as biomechanical strength or growth-inducing properties; effectiveness across a wide range of operating modifications and for a wide variety of tissue types; ability to conclude the process in a final implant tissue container, to ensure sterile packaging and delivery for implantation.

SUMMARY OF THE INVENTION

This invention provides a process wherein an oscillation of pressure is created in a chamber containing an implant material in the presence of various cleaning solutions (0.5% tri( n-butyl)phosphate, TNBP; hydrogen peroxide and the like). The process essentially comprises the following steps, assuming a metallic or synthetic material having an internal matrix or space, or manually cleaned (debrided) graft material, which may or may not have undergone initial machining, is used as the starting material:

1. Rapidly evacuate the chamber containing the implant, autograft, allograft or xenograft material;
2. Rapidly backfill the chamber with cleaning solutions—e.g. $H_2O_2$/Triton X-100/TNBP/Betadine mixtures;
3. Pressurize chamber;
4. Rapidly cycle between steps (1) and (3), for between about 1–150 cycles, maintaining a temperature of between about 35–40 degrees centigrade, with optional application of ultrasonic energy;
5. Machine the product as desired if not previously machined;
6. Repeat steps (1)–(4) using the same or a different cleaning compositions, optionally under elevated or reduced temperature; and
7. Optionally perform a surface decontamination step, preferably in the final packaging, as in exposure to vapor phase $H_2O_2$ or like surface decontamination treatments known in the art.

The absolute pressures of the system do not appear to be extremely critical to achieving deep, penetrating cleaning of the implant or graft materials. Rather, it is the rate of pressure cycling, the fact of cycling, and possibly the amplitude of pressure cycling, that appears to be critical to the success of this method. Accordingly, the entire process may be successfully conducted at pressures above or below one atmosphere. Evacuation pressures of 25 inches of mercury to the vapor pressure of the solutions in the chamber are adequate. Backfill pressures of between about 40 and 100 PSI are also adequate. Preferably, the entire process is conducted in a chamber which permits for sonication of the contents throughout or at particular stages of the process. In addition, preferably, the entire process is conducted in a programmable system under computer or programmable logic circuit control, so that manual processing is minimized and reproducibility of the process is maximized. Where the processed tissue is a bone implant or any form of allograft or xenograft tissue, election of appropriate solvents, such as urea (preferably about 6 M), or other chaotropic reagents, (e.g. 4 M guanidine hydrochloride, or the like), has the additional advantage of producing a processed tissue of even lower antigenicity than if such treatment were not included. Target decontamination goals for this process include:

Between about a one (1) to twelve (12) log reduction in bacterial contamination

Between about a one (1) to fifteen (15) log reduction in enveloped virus contamination Up to about a five (5) log reduction in non-enveloped virus contamination Between about a two (2) to ten (10) fold reduction in endotoxin Maintenance of implant or graft biologic and biomechanical properties absence of tissue toxicity due to cleaning solutions used reduced implant antigenicity Accordingly, it is an object of this invention to provide a method for production of safe and effective allograft, autograft, xenograft, metallic or synthetic implants in an efficient, economical manner.

It is a further object of this invention to permit safe pooling of tissue donor sources for implant production, while minimizing the risk that any single contaminated donor will contaminate any other donor tissue or any recipients of the pooled tissue processed according to the method of this invention.

Another object of this invention is to provide a method for cleaning, perfusing or passivating implant materials without at the same time compromising the desirable biological properties of the starting implant materials.

A further object of this invention is to produce implant materials of reduced antigenicity.

Further objects and advantages of this invention will become apparent from a review of the complete disclosure, including the claims which follow.

BRIEF DESCRIPTION OF THE DRAWINGS

FIG. 1A provides a schematic in which the cyclic perfusion passivation process of the invention through seven cycles is shown, while FIG. 1B shows the cyclic pressure and fluid exposure to implant materials treated according to the method of this invention.

DETAILED DESCRIPTION OF THE PREFERRED EMBODIMENT

Figure 1:
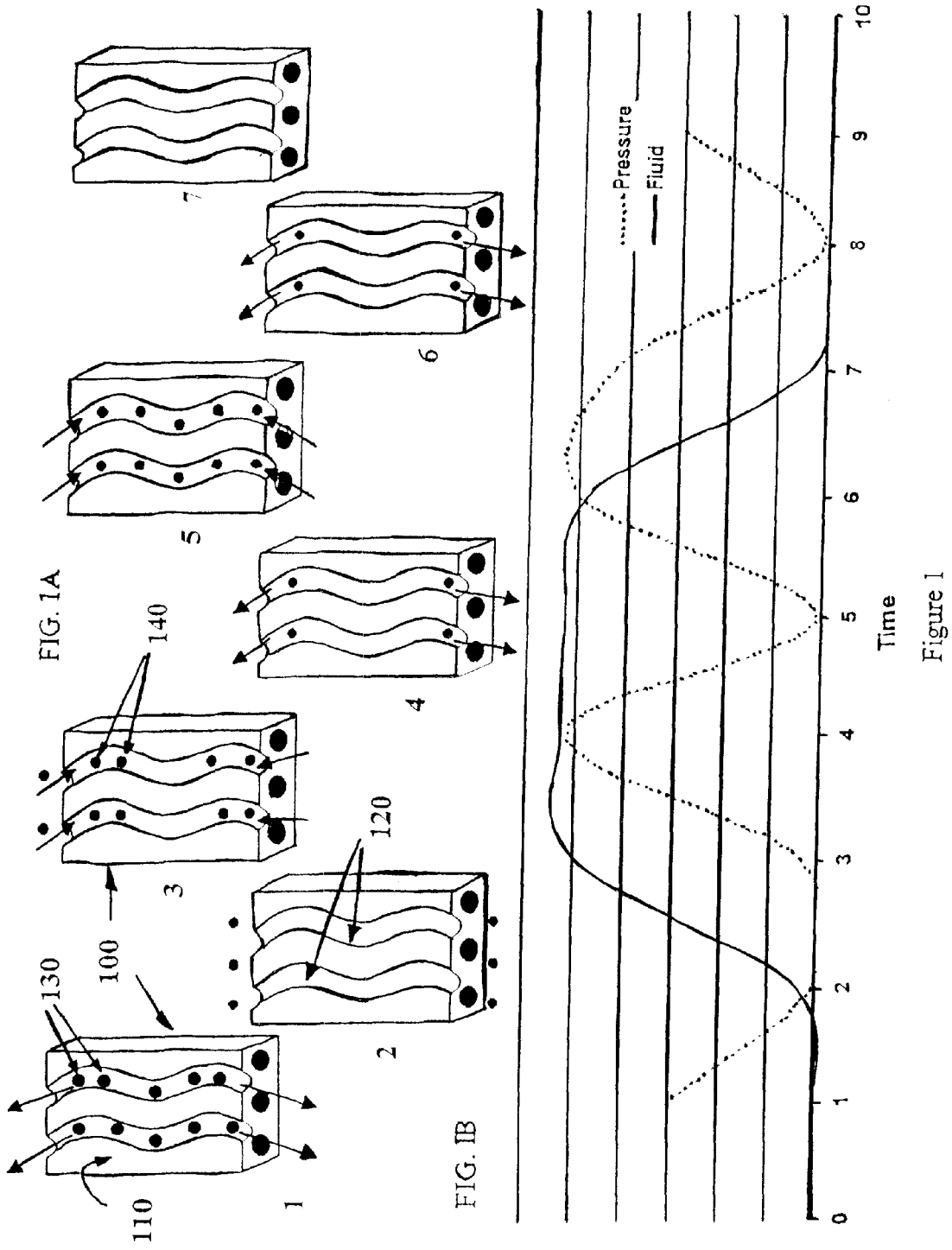

As used herein, the term "passivate" is intended to refer to the elimination of potentially pathogenic organisms and immunogenic substances from an implant. Thus, both sterility and reduced antigenicity is intended by this term, although elimination of beneficial biological properties of the implant, such as osteogenic properties (osteoconduction or osteoinduction; bone fusion), natural tissue functionality, and desirable structural strength of an implant are not intended by this term. The term "passivation" is preferred to the term "sterilize" because, while sterilization is a goal, that term has an absolute connotation which can rarely, if ever, be completely achieved without attendant tissue destruction. In addition, while the implants produced according to the method of this invention may not be completely devoid of any antigenicity or pyrogenicity, these undesirable aspects are greatly reduced, and this too is intended by the term "passivation," as used herein.

The terms "perfused" or "perfusion," as used herein, are intended to imply efficient interpenetration of cleaning solutions into and through the channels and crevices of materials intended for implantation into a recipient.

As used herein, the terms "rapid" or "rapidly" as they are applied to the process of pressure cycling according to this invention mean time frames on the order of seconds to minutes, rather than hours or days.

The terms "sonicate" or "sonication" as used herein mean the application of sonic or ultrasonic energy via a container of an implant undergoing processing according to the method of this invention under conditions that permit efficient transfer of the sonic energy to the implant. Those skilled in the art are familiar with the process of sonication and conditions whereby sonic energy may be transferred through a fluid to a workpiece such that efficient cleaning and bacterial or cellular disruption is achieved, without resulting in gross, ultrastructural damage to the workpiece.

This invention provides a novel method for processing implant materials including, but not limited to, metallic implants, synthetic implants, ceramic implants, autograft, allograft or xenograft materials, including bone and soft tissue. In particular, soft tissue or allograft bone materials treated according to the method of this invention permit soft tissue or debrided allograft, autograft or xenograft bone to be thoroughly cleaned, machined, sterilized, packaged and then implanted at economies of scale heretofore not possible. In the past, tissue banks have attempted, as much as possible, to process tissue from single donors, without permitting contact between tissue derived from different donors. The concern has been that any given donor tissue may contaminate other donor tissue. Due to the extreme value of any donor's tissue, the risk of a large batch of donor tissues being found to be contaminated has been considered an unreasonable risk. However, according to the method of the present invention, even if heavily contaminated donor tissue is included in a batch of pooled donor tissue, the resultant graft material available for implantation is safe for implantation.

Methods for minimizing the risk that donor tissue will be harvested and processed by a tissue bank, referred to herein as "donor qualification", are known in the art. Accordingly, thorough donor screening, and tissue testing by enzymatic, immunological, biochemical and molecular biological techniques are applied to minimize the risk that tissue carrying pathogens (viruses, bacteria, and the like) will be included in the materials processed and made available for implantation. Testing for contamination by human immunodeficiency virus, HIV, hepatitis B virus, HBV, hepatitis C virus, HCV, has now become routine in the art. Known screening and qualification methods are desirably included as an initial step preceding processing of the implant material according to the present method. Due to the highly efficient implant cleaning, permeation and passivation process encompassed by the instant invention, it is further expected that as yet unidentified potentially pathogenic organisms or organisms for which routine testing has yet to be developed will, in any event, be removed from implant materials by virtue of the instant implant treatment process. Redundancy in the level of implant cleaning that is built into the instant pressure cycling permeation and passivation process ensures inactivation of such organisms while at the same time permitting efficient implant processing.

For purposes of the following description, allograft bone is referred to as an exemplary tissue that may be processed according to the present method. However, those skilled in the art will recognize that other tissues, including but not limited to autograft bone, xenograft bone, other porous tissues, synthetic porous materials, and various soft tissues, may be processed according to the principles defined herein, without departing from the spirit of the invention exemplified herein by reference to allograft bone material.

According to this invention, allograft bone material from qualified donors is first treated by various known bioburden reducing methods, as in cleaning by debriding adventitious tissue according to methods known in the art. Manual dissection may be employed for removal from the bone surfaces of ligaments, tendons, skin, fat, muscle, loose bone marrow, and any other non-bone tissue. Alternatively, automated or semi-automated methods known in the art, (see, for example, the methods disclosed in U.S. Pat. Nos. 5,333,626; 5,513,662; 5,725,579, and the like, herein incorporated by reference for this purpose), may be employed for initial cleaning of the donor bone material.

At this stage of the process, the cleaned allograft materials from individual donors may be pooled and further cleaned as described below. Alternatively, the allograft bone may be machined to the final implant dimensions, followed by pooling with a batch of similarly processed, dimensioned implants for further cleaning as described below. For tracking purposes, while individual donors would have been tracked up to this stage, upon pooling, a batch number is defined for further racking, with records being maintained of all of the donors that have contributed to the batch. In yet a further alternative, and to ensure redundancy in the level of cleaning and potentially pathogenic contaminant inactivation, implant materials from individual donors may first be treated as described below, prior to pooling with implant materials from different donors. In this event, the implant material form individual donors may be further cleaned whole or first machined to desired final dimensions.

When applied to bone, subsequent to initial bioburden reduction and surface cleaning, the method of this invention provides for further processing whereby bone marrow, blood, proteins, and particulate matter is efficiently removed, such that what remains is essentially a mineralized collagen matrix, in which about a 5 to 6 log reduction in any form of viable organisms (viruses, bacteria, amoebae, rickettsia, fungi) is achieved. As described in greater detail below, this is achieved by a process of pressure cycling or oscillation, employing a variety of cleaning and sterilization solutions which are caused to efficiently interpenetrate the matrix. By repeated cycling and changing of the cleaning solvents, the channels of essentially any porous matrix are unclogged, and cleansed. A pre-defined, pre-programmed cycle of washes is employed, preferably with concurrent ultrasonic bombardment, to achieve penetrating sterilization of the implant. We have found that the combination of oscillating fluid pressure and ultrasonic energy accelerates solution interpenetration and endogenous substance removal.

In view of the foregoing description, it will be appreciated that in one embodiment, the invention is a method which comprises the following steps:

1. Rapidly evacuate a chamber containing the implant such as porous metallic or synthetic materials, autograft, allograft or xenograft;

2. Rapidly backfill the chamber with cleaning solutions—e.g. $H_2O_2$/Triton X-100/TNBP/Betadine mixtures;

3. Pressurize chamber;

4. Rapidly cycle between steps (1) and (3), for between about 1–150 cycles, maintaining a temperature of between about 35–40 degrees centigrade, with optional application of ultrasonic energy;

5. Machine the product as desired if not previously machined;

6. Repeat steps (1)–(4) using the same or a different cleaning compositions, optionally under elevated or reduced temperature; and 7. Optionally perform a surface decontamination step, preferably in the final packaging, as in exposure to vapor phase $H_2O_2$ or like surface decontamination treatments known in the art.

The process of perfusion passivation is further defined with reference to FIG. 1A. This schematic shows an implant 100 comprising solid structural constituents 110, channels 120, and adventitious materials 130 embedded within the channels 120. The structural constituents 110 may be synthetic materials, as in man-made polymeric material, (e.g. poly-L-lactic acid, acrylic acids, and the like), metallic structural materials, or natural materials, such as a mineralized or demineralized collagen matrix. The channels 120 may be man-made channels, defined by the polymerization, molding, melting or other manufacturing process, or may be natural channels, such as those found in mineralized or demineralized cancellous or cortical bone matrices. The adventitious materials 130 may be cellular debris, bone marrow, cells, lipids, carbohydrates, proteins, viruses, bacteria, rickettsia, amoebae, fungi and the like. In FIG. 1A, panels (1) and (2) relate to the first step described above. In panel (1), the channels 120 are primed for back-filling with cleaning solutions by exposing the tissue to decreased pressures. In panel (2), the cleared channels 120 are shown to be substantially clear of adventitious materials 130. Panel (3) relates to steps 2 and 3, wherein molecules of cleaning solution 140 are introduced into a sealed chamber and are driven into the channels 120 by elevated pressures. Panel (4) relates to the fourth step described above, wherein decreased pressure removes remaining cellular debris, cleaning solution 140, and other remaining adventitious materials from the channels 120, and again primes the matrix for deep penetration, now possible due to the clarity of the channels 120. In panels (5)–(7), a one cycle repeat according to the fourth step described above is shown, whereby upon repressurizing with clean solvents, full interpenetration of the solvents into the implant matrix is achieved. In panel (6), reduced pressure draws the remaining solution from the implant, which may then be dried, as shown in panel (7), prior to further processing (e.g. machining according to step 5 above, further cleaning, according to step 6 above), and final packaging of the cleaned tissue. The cycle depicted in FIG. 1A may be repeated as many times as desired to ensure complete internal cleaning of the matrix interior. In FIG. 1B, a representation of the pressure and fluid oscillation throughout the various steps of the above described process is represented.

After being medically released, (i.e. passing a battery of risk factor and biochemical assays, including, for example, HIV-specific PCR, and the like), donor tissue is cleaned of any extraneous or adventitious tissue. The thus-cleaned tissue is loaded into a sealable reaction chamber. A preferably pre-programmed tissue cleaning process is then initiated comprising a plurality of wash steps. Deep tissue interpenetration by cleaning solutions is achieved by oscillating the pressure in the chamber while adding and removing various cleaning solvents. Ultrasonic energy is applied at various stages of the cleaning process to accelerate solution penetration and removal of unwanted contaminants or endogenous substances, including blood, lipid, and non-structural or undesired proteins. In one preferred cleaning cycle according to this invention, a steps (1–4) of the claimed process are carried out according to a protocol similar to that defined in the following table to remove blood, fat, bacterial, viral, fungal or other contamination:

According to Table I, in step 0, under atmospheric pressure, and no fluid or sonication, a pressurizable chamber in which the process may be conducted, is loaded with metallic, synthetic or other man-made implant materials, allograft bone or soft tissue, xenograft bone or soft tissue, from an individual qualified donor. Where the implant is a tissue, the tissue is preferably first cleaned of surface adventitious tissue, prior to initiating the steps shown in table I. In step 1, under negative pressure (vacuum), for a period of about two minutes, the matrix of the implant or implants is primed (i.e. see FIG. 1, step 1, to remove trapped air, cellular and other loose debris by vacuum). In step 2, under negative pressure, cleaning fluid is introduced with sonication, to aid in penetration of the fluid and to ensure gas is removed from the introduced fluid. In step 3, under positive pressure, and in the presence of an appropriate cleaning solvent and sonication, solvent is forced into the matrix of the implant. Thereafter follows a series of "n" cycles of positive and negative pressure in the presence of solvent and sonication, during which the matrix channels are backfilled and emptied of solution and debris. The number of times this step is cycled may be from once to about 150 times (i.e. n =1–150; preferably n is about 10–50 times).

After step 4 in Table I, the cleaning fluid is removed to waste under positive pressure, the tissue is dried under negative pressure, and is rinsed several times under oscillating positive and negative pressure using sterile water or physiological saline (e.g. phosphate buffered saline, PBS), with or without accompanying sonication. The number of rinse cycles may be from 1–150 times, and is preferably about 1–50 times. The rinse solution is drained under positive pressure, and the tissue is again dried under negative pressure.

After removal of the gross contamination according to the steps outlined above, the tissue in-process may be machined into dimensionally finished grafts if such processing has not previously been accomplished, (step 5 of the instant process, as defined above), and then loaded into a reaction chamber, same or different than that used to carry out the steps according to Table I. A deep-penetrating cleaning, passivation or sterilization cycle, preferably under programmable logic control, is then conducted according to a protocol similar to that defined in Table II (see step 6 defined above, which represent a repeat of steps 1–4 of Table 1, optionally using different cleaning solvents; these steps are distinguished by indicating the steps as 0'–4'):

TABLE I

| Step | Pressure | Fluids* | Sonication | Duration (min) | Purpose |
| --- | --- | --- | --- | --- | --- |
| 0 | Atmospheric | None | Off | NA | Load tissue into chamber |
| 1 | Negative (60–100 torr) | None | Off | 2 | Prime tissue matrix, remove included air and loose debris |
| 2 | Negative (60–100 torr) | B, C, D, E, mixtures | On | 1 | De-gas cleaning fluids |
| 3 | Positive (5–8 atmospheres) | B, C, D, E, mixtures | On | 1 | Force fluids into tissue matrix |
| 4 | Negative/Positive | B, C, D, E, mixtures | On | (1 × n) | Remove debris loosened by fluids, pressure oscillation and sonication |

*Fluids:
B = Triton X-100/TNBP, a solvent/detergent to remove debris and kill viruses and bacteria;
C = 3% hydrogen peroxide, to remove cellular debris, inactivate viruses and bacteria;
D = mixture of B and C;
E = water-miscible alcohol, such as ethanol or isopropanol;
mixtures = B, C, D, E in any desirable proportions.

TABLE II

| Step | Pressure | Fluids* | Sonication | Duration (min) | Purpose |
|---|---|---|---|---|---|
| 0' | Atmospheric | None | Off | NA | Load tissue into chamber |
| 1' | Negative (60–100 torr) | None | Off | 2 | Prime tissue matrix, remove included air and loose debris |
| 2' | Negative (60–100 torr) | F, G, H, I, J, mixtures | On | 1 | De-gas cleaning fluids |
| 3' | Positive (8–10 atmospheres) | F, G, H, I, J, mixtures | On | 1 | Force fluids into tissue matrix |
| 4' | Negative/Positive | F, G, H, I, J, mixtures | On | (1 × n) | Remove debris loosened by fluids, pressure oscillation and sonication |

*Fluids:
F = 6M urea or other chaotropic agents, e.g. 4 M guanidine HCl, to reduce implant antigenicity;
G = 1% sodium hypochlorite, to inactivate viruses, bacteria, fungi or other residual contaminants;
H = 1N sodium hydroxide, to inactivate viruses and bacteria;
I = 6% hydrogen peroxide, as a sterilant;
J = hexane, ether, diethanolamine (DEA), toluene, xylene, butane, $CO_2$ (supercritical), isobutane, propane, acetone, isopropanol, methanol, ketones, ethers, aliphatic or aromatic hydrocarbons, HCl, gasseous HCl.
mixtures = F, G, H, I, J in any desirable proportions.

After step 4' in Table II, the cleaning fluid is preferably retained in a positively pressurized reaction chamber for an extended period to ensure complete killing of any residual contaminating pathogens or other organisms. A period of from one to sixty minutes, and preferably about ten minutes, is sufficient for this purpose. The cleaning fluid is then removed to waste under positive pressure, the tissue is dried under negative pressure, and is rinsed several times under oscillating positive and negative pressure using sterile water or physiological saline (e.g. phosphate buffered saline, PBS, or the like), with or without accompanying sonication. The rinse solution is drained under positive pressure, and the implant is again dried under negative pressure.

Those skilled in the art will appreciate that the specifics of the process outlined according to Tables I and II above may be modified, without departing from the essence of the present invention. Essentially, other cleaning solvents or concentrations than those suggested herein may be used, the number of oscillations between elevated and reduced pressure, and the cycling times, pressurization and depressurization levels and periods may be altered, according to the requirements for a given tissue. However, the conditions specified in Tables I and II result in deeply penetrating cleaning, as evidenced by the ability to force dyes deep into tissue matrices, to remove dyes that have been allowed to soak deep into tissue matrices, and the ability to remove or kill endogenous or added biological contaminants, including a wide variety of bacteria, viruses and fungi. Tissues cleaned according to this procedure include, but are not limited to: cortical bone, cancellous bone, fascia, whole joints, tendons, ligaments, dura, pericardia, heart valves, veins, neural tissue, submucoal tissue, (e.g. intestinal tissue), and cartilage. Bone treated according to this method and subsequently tested for retained biomechanical strength and ability to induce new bone formation (osteoconduction and osteoinduction, collectively referred to as osteogenic activity) retains good biomechanical strength and is expected to retain osteogenic activity. Furthermore, bone treated according to one embodiment of this method and implanted as a xenograft was found to induce little or no adverse immunological reactivity, indicating reduction in antigenicity of the material. This is particularly true where urea or other chaotropic agents (e.g. guanidine hydrochloride), is used as one of the cleaning fluids or is included in a mixture of cleaning fluids.

Figure 2:
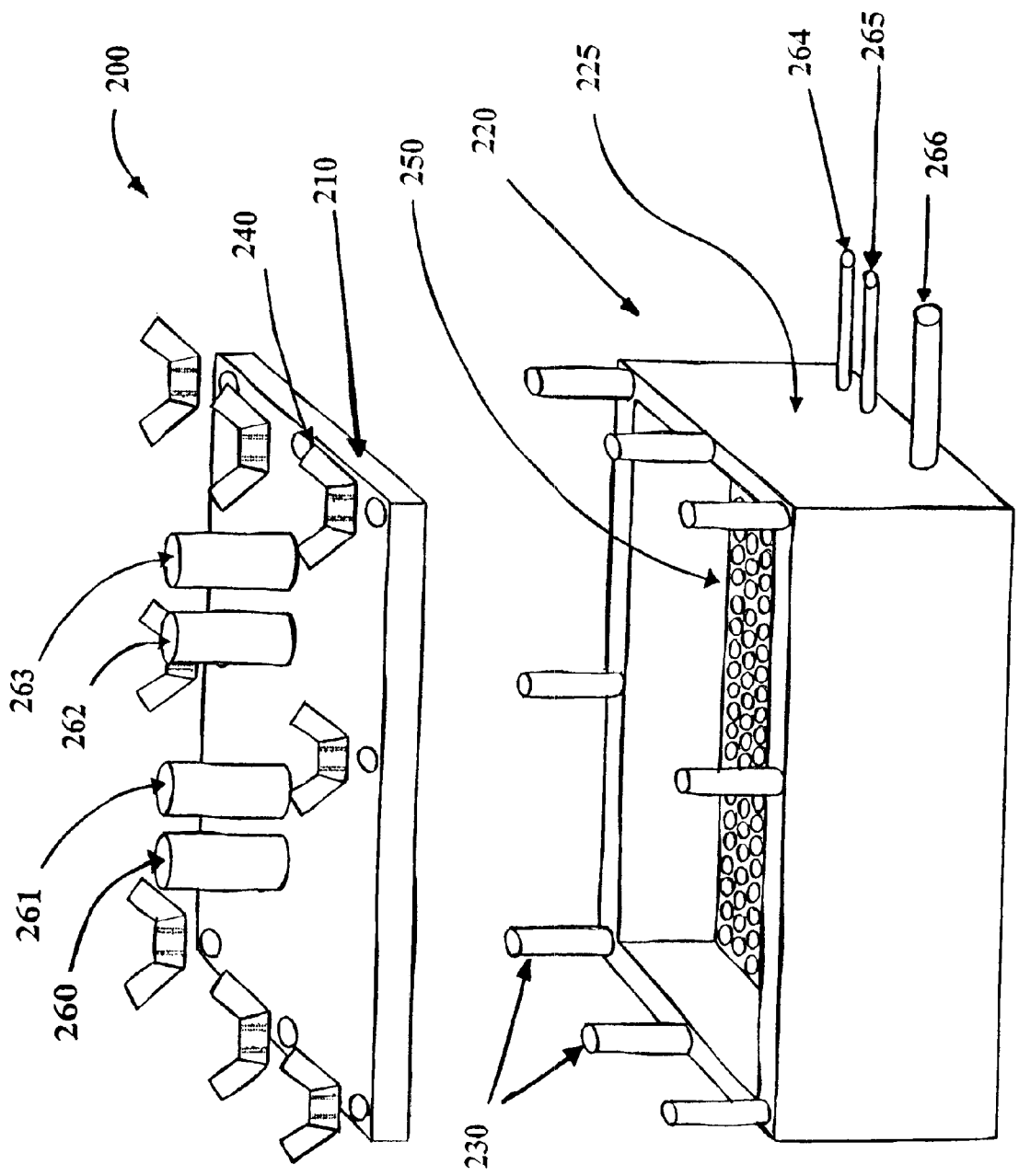
FIG. 2 shows a schematic of one embodiment of an apparatus that may be employed to effect the method according to this invention.

The method disclosed herein will suggest to those skilled in the art a number of possible devices to achieve the programmed steps defined above. Thus, for example, in one embodiment according to this invention, a device such as that shown schematically in FIG. 2 may be employed for semi-manual implementation of the cyclic perfusion passivation process of this invention. According to this embodiment of the invention, a chamber 200 comprising a lid 210 and a trough 220 is adapted for cyclic perfusion passivation of implants. A series of posts 230, onto which a series of bolts 240 may be tightened are provided for securing the lid 210 to the trough 220. A grating 250 is provided inside the chamber 200 for receiving implant material to be treated. Through the lid 210 is provided a series of access ports 260,261,262,263. Access port 260 is a sterile water input line. Access port 261 is an input line for other fluids. Access port 262 is a vacuum line. Access port 263 is a line for pressure input. In addition, a port 264 is provided for insertion of a temperature probe. Port 265 is a port for supplying power to a sonicator built into the walls 225 of the chamber 200. Port 266 is a drain. Accordingly, a device such as that shown in FIG. 2 could be used carrying out the cyclic perfusion passivation process according to this invention.

Figure 3:
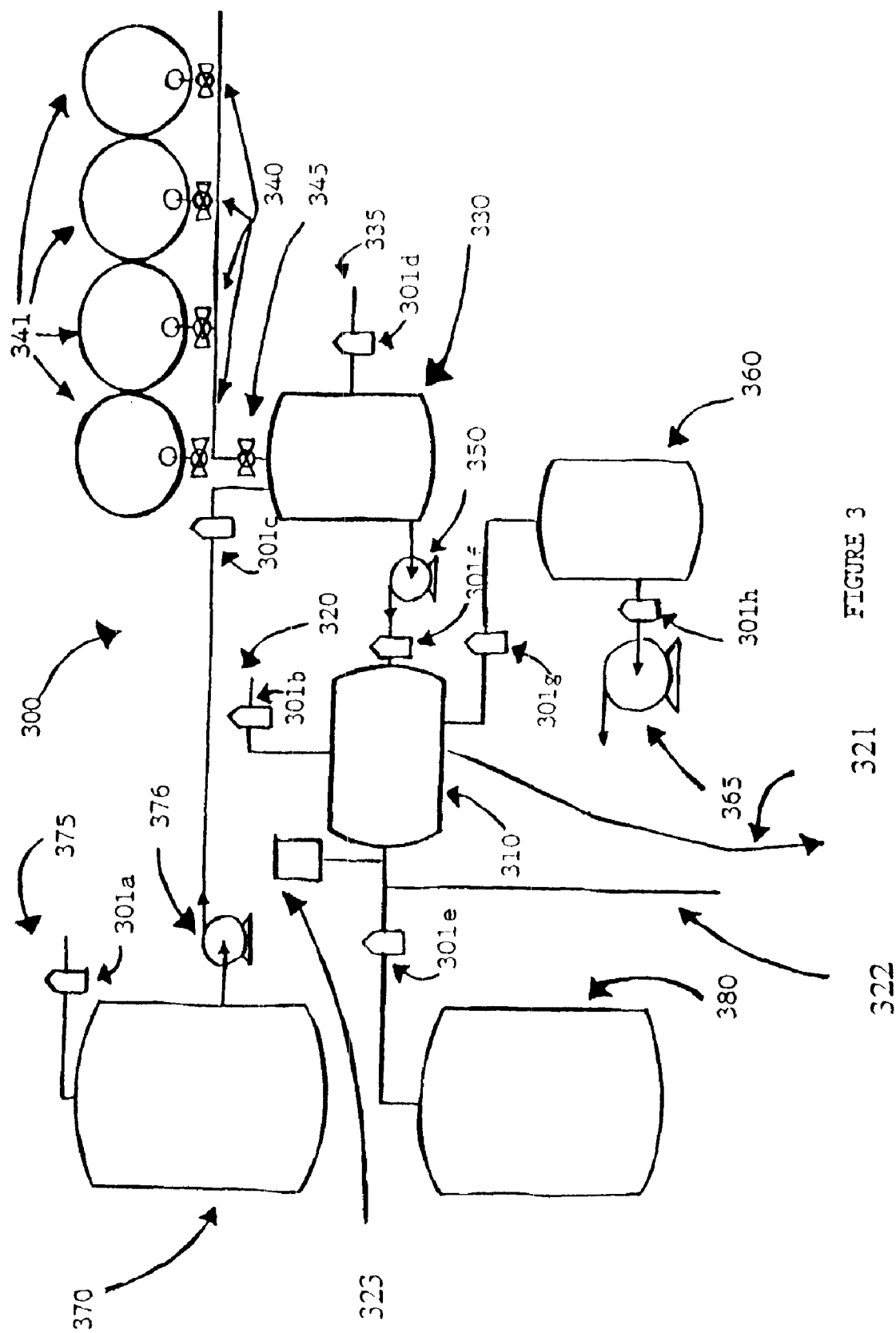
FIG. 3 shows a schematic representation of a further embodiment of an apparatus layout for conducting the method according to this invention.

With reference to FIG. 3, an automated or semi-automated apparatus 300 may be defined for carrying out the instant process. Per this disclosure, programmable logic controllers activate or deactivate valves or solenoids 301a–h at predetermined times in the cleaning cycle. An implant is placed in a reaction chamber 310 which is sealed. An atmospheric vent 320 is provided to permit entrance and removal of waste and filtered air. Cleaning fluids are introduced into reaction chamber 310 from a chemical mixing tank 330 which has a filtered vent to atmosphere 325, to avoid formation of a vacuum in the tank 330. Chemical feed lines 340 lead from fluid reservoirs 341 to the chemical mixing tank 330 via a common conduit 345. A programmably controlled pump 350 is operated to pump appropriately mixed fluids from the tank 330 into the reaction vessel 310. Vacuum or negative pressure is applied to the reaction vessel 310 by means of a vacuum receiver tank 360, in which a source of negative pressure is created by vacuum pump 365. The inclusion of a vacuum reservoir 360 is desirable so that essentially instantaneous vacuum of known dimensions may be applied to the reaction chamber 310, without the need for a vacuum pump such as 365 having to gradually develop the negative pressure. Vacuum receiver tank 360 may be evacuated by pump 365 while reaction tank 310 is under positive pressure. A source of sterile water, physiological saline, or like aqueous solution is provided in storage tank 370, which has a filtered vent 375 to prevent formation of a vacuum in tank 370. Pump 376 provides for rapid infusion of aqueous solution into chemical mixing tank 330 for introduction into the reaction chamber 310. Those skilled in the art will appreciate that the water from tank 370 may also be directly introduced into reaction tank 310, without having to first be introduced into chemical mixing tank 330. Positive pressure is stored in pressure tank 380 which is pressurized by a compressor of filtered gas, to retain sterility in the reaction tank 310. In practice, an appropriately programmed computer or programmable logic controllers permit venting of the reaction chamber 310, to permit loading of tissue. The chamber is then sealed, evacuated, pressurized, and fluid is introduced and removed, as outlined, for example, in Table I and Table II above, to complete the implant cleaning process.

Manual or automated perfusion of cleaning and sterilizing fluids, as outlined above, results in reduction of the bioburden of implant material from individual donors, prior to pooling with implant materials from other donors for batch processing. Initial bioburden reduction may be achieved according to a protocol such as that outlined in Table I, to reduce the potential for contamination of an uncontaminated implant by contact with a contaminated implant. However, those skilled in the art will recognize that the penetrating passivation process of this invention is so efficient that for certain types of implants in which the initial prospect of encountering a contaminated implant is sufficiently low, it may be possible to simply batch process implant materials according to Table I and Table II, rather than first cleaning implants from an individual donor according to the Table I program, prior to combining such implant materials from different donors and processing the pooled implants according to the Table II program.

Where an initial bioburden reducing step for implant materials derived from individual donors is considered prudent, individual donor tissues are processed according to the Table I program, and are then quarantined until all quality control criteria are passed. Only the individual donor tissues that pass such quality control after initial bioburden reduction are pooled for processing according to the Table II protocol. As an initial bioburden reduction program, a combination of TritonX-100 and TNBP may be used as a first solvent to remove debris and to inactivate bacteria and viruses. A second solvent may be a 3% hydrogen peroxide solution to remove cellular debris and to further reduce bioburden. A third solvent may be povidone iodine solution to yet further reduce bioburden. Finally, ascorbic acid solution may be employed to decolorize the implant or remove any residual iodine. These solutions may be employed in a different order, and indeed, different solutions may be used to similar effect. The particular solutions listed are preferred, however, due to their low toxicity, and our discovery that the defined combination of solutions results in efficient reduction in bioburden, implant cleaning, passivation and interpenetration. The solutions of Table I are typically employed in a cycle such as that shown in Table I, steps 0–4.

At this stage of the process, cleaned allograft or xenograft tissue from individual donors or previously pooled donors is optionally pooled and further cleaned as described below. Alternatively, the tissue is first dimensioned by machining, trimming and the like, to achieve the final implant dimensions. The dimensioned tissue is further processed individually or is pooled with a batch of similarly or differently processed, dimensioned implants for further cleaning as described below. For tracking purposes, while individual donors would have been tracked up to this stage, upon pooling, a batch number is defined for further tracking, with records being maintained of all of the donors that have contributed to a given batch.

In Table II, a set of solutions is described for achieving penetrating sterilization of individual tissues or tissues pooled from different donors which have already been treated according to the program outlined in Table I. Thus, a first solution of 6% hydrogen peroxide, followed by a second solution of 1% sodium hypochlorite, followed by a solution of 1 N sodium hydroxide, may be used to achieve sterilization. A 70% solution of isopropanol may be used as a broad spectrum germicide. Thus, the solutions of Table I and Table II may be employed according to the program shown, or modified as needed. Those skilled in the art will appreciate that different penetrating sterilants may be employed or that mixtures of the described sterilants may be possible. In any event, at the conclusion of this stage of the process, the individual or pooled batch of implants has been thoroughly cleaned, passivated (if not sterilized), and interpenetrated by cleaning solutions. Reductions in enveloped virus, vegetative bacteria, and fungal contamination of up to twelve logs or higher and of non-enveloped viruses and spores of up to about five logs are achieved according to the process described herein. In addition, about a two to ten-fold reduction in endotoxin levels is achieved, along with significant elimination of blood, lipid, nucleic acid, and non-structural protein. Furthermore, this process retains the beneficial structural and other desirable biological properties of the implant material. Significant enhancements in production yields, through the ability to batch process implant from pooled donors, are also achieved.

Subsequent to penetrating passivation of the implant materials, the implant materials are placed in their final packing. Preferably, this is achieved in a sterile environment to avoid introduction of any adventitious bioburden. To ensure sterile packaging, with the final machined grafts in their final, unsealed packages, the implants are exposed to a vapor-phase hydrogen peroxide/peracetic acid or like vapor-phase sterilizing environment. The packages are then closed to ensure that no contamination may occur upon removal of the implants from the sterile field for storage or shipment to surgeons. The sealed packages may then, optionally, be subjected to levels of gamma or other types of irradiation known to not adversely affect tissue properties (e.g. below about 3.0 Mrad, or for short periods of time to effect surface sterilization, and to ensure internal destruction of any residual large-genome organisms; however, such internal treatment is generally not required, deep sterilization having been achieved according to the cleaning protocol described herein). Other surface and redundant internal sterilization methods, including exposure to electron beams, exposure to ethylene oxide, and the like, may also be conducted at this stage, so long as toxicity or diminishment of desirable biological activities is not thereby effected.

As a further enhancement to the process defined herein is the ability to produce implant materials with perfusion of desirable bioactivities. Accordingly, in the final rinse steps after steps 0–4 or Table I or steps 0'–4' of Table II, a solution containing desired antibiotics, anti-inflammatory drugs or other biologically active agents may be employed to infuse antibiotic or other desired bioactive substances into the cleaned, passivated tissues. Alternatively or in addition, growth factors, such as bone morphogenetic proteins, cartilage derived growth factors, tissue growth factors, natural or recombinant, and the like known in the art may be perfused into the implant.

As can be appreciated from the foregoing detailed disclosure, the process of the present invention may be carried out at any stage of implant production, and it does not require special preparations such as removal of cartilage, or potentially implant damaging steps such as drilling of holes.

Figure 4:
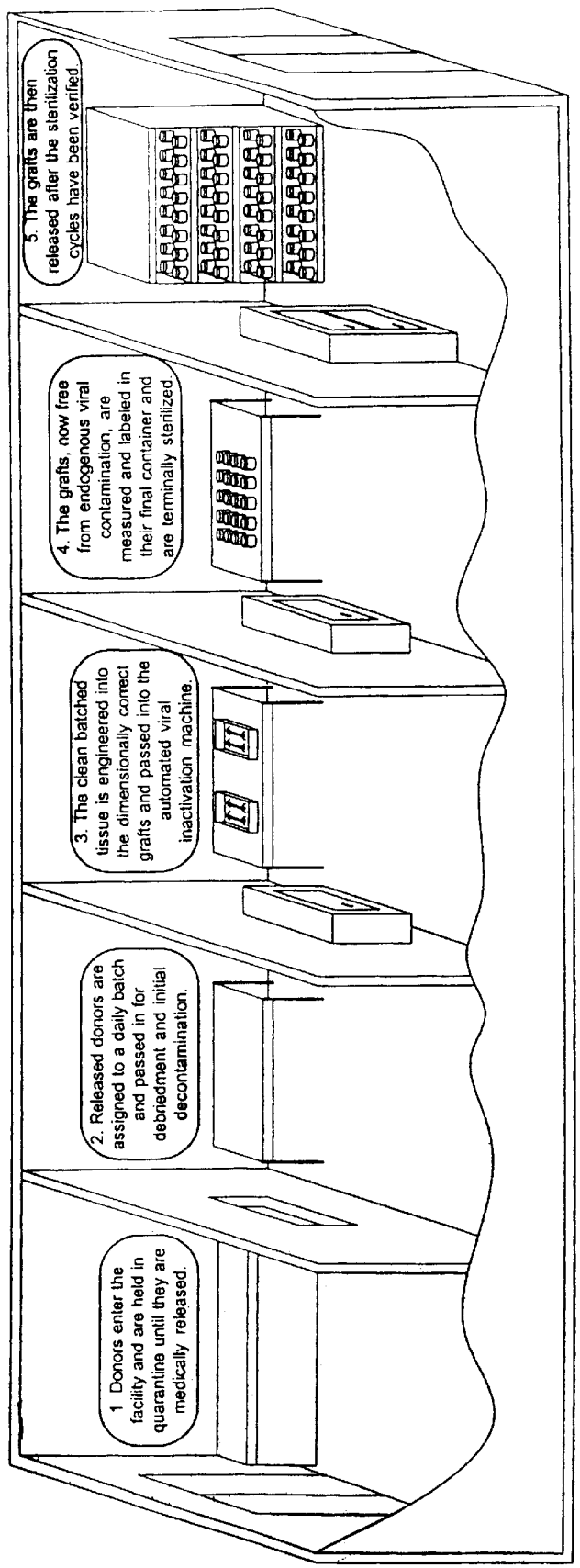
FIG. 4 provides an overall flow-chart of the various stages of processing an implant according to the cyclic perfusion passivation process of this invention from donor tissue acquisition through final sterile product packaging.

As a means of providing an overall concept of the flow of the method according to the present invention, the schematic provided according to FIG. 4 is described. In stage 1, donor materials are introduced into the donor tissue processing facility and are held in quarantine until the donor from which the tissue was derived is qualified. In stage 2, released donor materials are surface cleaned by debridement. In stage 3, surface cleaned tissue is machined to produce implants of the desired final dimensions, and are introduced into an automated cyclic perfusion passivation chamber according to the present invention. In stage 4, implants that have been passivated are introduced into their final packing containers and are terminally sterilized by gamma irradiation, vapor-phase exposure to decontaminants, and the like. Finally, in stage 5, the passivated and packaged grafts are stored and released after verification of the sterilization cycles.

Figure 5:
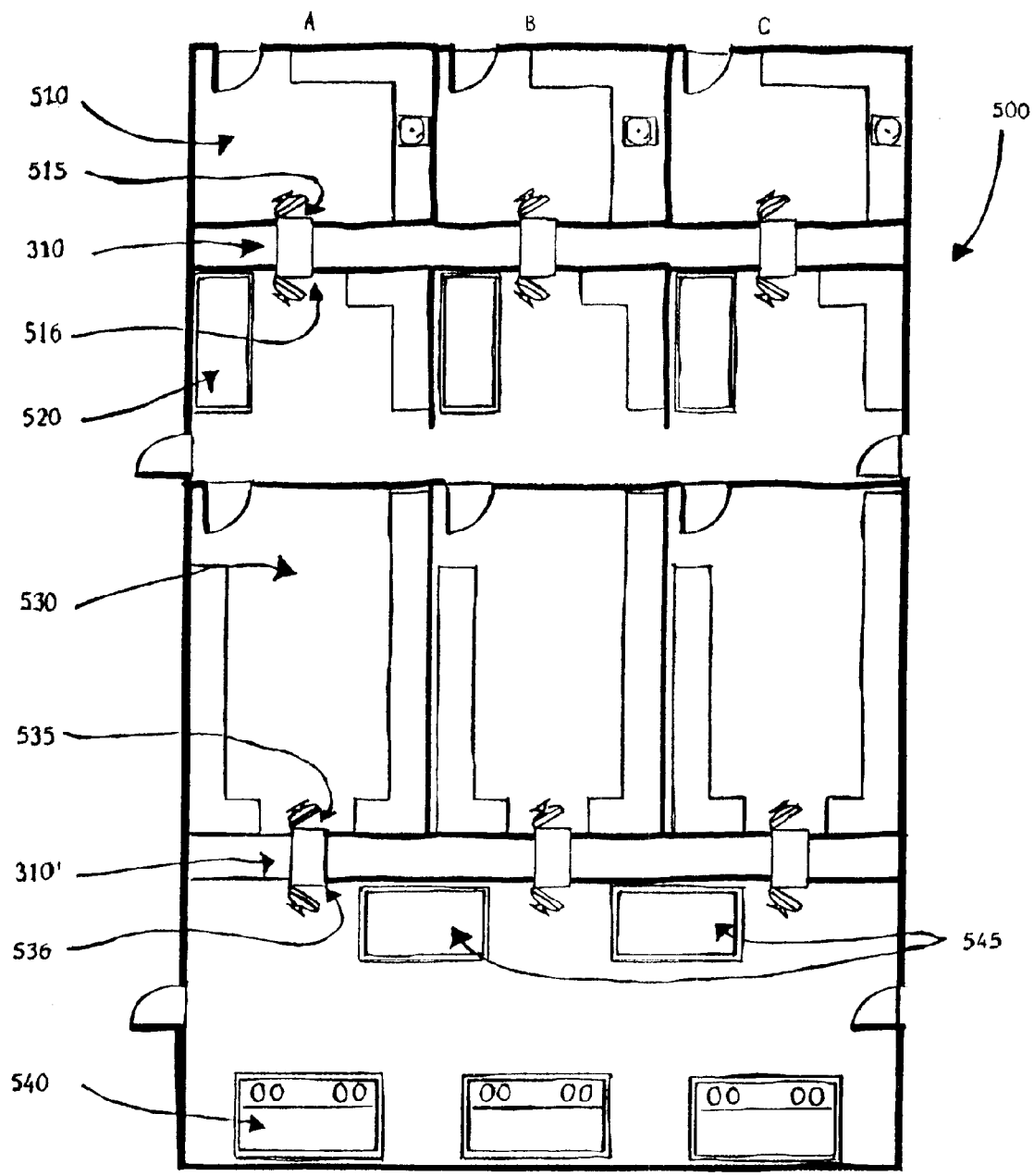
FIG. 5 provides one embodiment of a detailed processing containment layout for conducting the method according to this invention.

In a further embodiment of this invention, a process layout similar to that shown schematically in FIG. 5 may be employed. According to this layout, a processing facility 500 shows three parallel and identical tissue processing facilities A–C. Starting in debridement chambers 510A–C, tissue to be treated according to this invention is cleaned and debrided of gross, adventitious and unwanted tissues. The cleaned tissue is then introduced, via sealable port 515A–C into a reaction chamber 310A–C, to which are connected all of the process control and input/output devices shown in FIG. 3. Upon completion of a cleaning cycle such as that defined according to Table I, tissue is removed via sealable port 516A–C. The cleaned tissue is sorted and stored in quarantine freezers 520A–C, until quality control demonstrates that the tissue is fit for further processing. The released tissues are then transferred to graft-production rooms 530A–C, where final implant dimensioning and machining is conducted. Following production of the finally dimensioned implants, the thus processed tissues are loaded into reaction chambers 310'A–C via sealable port 535. Not shown but connected to reaction chamber 310'A–C are all the process control and input/output devices shown in FIG. 3. Following further cleaning, such as that defined according to Table II, the deeply sterilized tissues are removed from sealable port 536A–C, and are placed in final packaging. Terminal sterilization is conducted at stations 540A–C, and the terminally sterilized tissues are sealed in the final packaging. The sealed packages of terminally sterilized tissues are quarantined in freezers 545 until final quality control testing permits tissue release to surgeons.

It will be appreciated that while the process layout provided in FIG. 5 is preferred, it is suggestive only, and the process according to the instant invention may be conducted in other layout formats. Further, it will be appreciated that according to the layout shown according to FIG. 5, it is desirable for the level of ambient particulates to be reduced as tissue is processed through the various stages shown. Thus, while it is adequate for the chamber 510 to be of class 100,000 (100,000 particles per billion), it is desirable for areas 520 and 530 to be class 10,000 or lower. The final packaging area 540 is preferably about a class 1000 area.

Having generally and in detail described this invention, including its best mode, the following specific examples are provided to further exemplify, but not to limit, the disclosed invention, the scope of which should be reviewed by reference to the claims appended hereto and the equivalents thereof.

EXAMPLES

Example 1

Specific Cleaning Protocol for Bone

In one preferred embodiment of this invention, an intact or machined bone implant is cleaned by treatment sequentially with povidone-I, water, ascorbic acid, TNBP/hydrogen peroxide, water, diethanolamine, water, 6 M urea, water. The sequence of sonication, and pressure fluctuations is conducted according to the sequence defined in Table I or Table II. It will be appreciated from this disclosure, however, that a wide variety of different cleaning solutions and combinations thereof may be employed according to the method of this invention. For example, the cleaning solutions may include: sterile water, Triton X-100, TNBP, 3% hydrogen peroxide, a water-miscible alcohol, saline solution, povidone iodine, ascorbic acid solution, aromatic or aliphatic hydrocarbons, ethers, ketones, amines, urea, guanidine hydrochloride, esters, glycoproteins, proteins, saccharides, enzymes such as proteases (trypsin, pepsin, subtilisin), lipases, sachrases, and the like, gasseous acids or peroxides, and mixtures thereof. The process is conducted at ambient temperatures, elevated temperatures (eighty degrees centigrade) or decreased temperatures. Thus, cleaning of implants in a liquid nitrogen phase (negative eighty degrees centigrade) is contemplated by this invention.

Example 2

Effectiveness of Process for Implant Cleaning

Figure 6:
FIG. 6 is a photograph of a whole humerus after being treated according to the method of this invention; a post-cleaning coronal section through the head of the humerus reveals the cleanliness of the inner bone matrix.

FIG. 6 is a photograph of a whole humerus after being treated according to the method of this invention; a coronal section through the head of the humerus reveals the cleanliness of the inner bone matrix.

Example 3

Effectiveness of Process for Cleaning of Hard Tissue and Soft Tissue Implants

Figure 7:
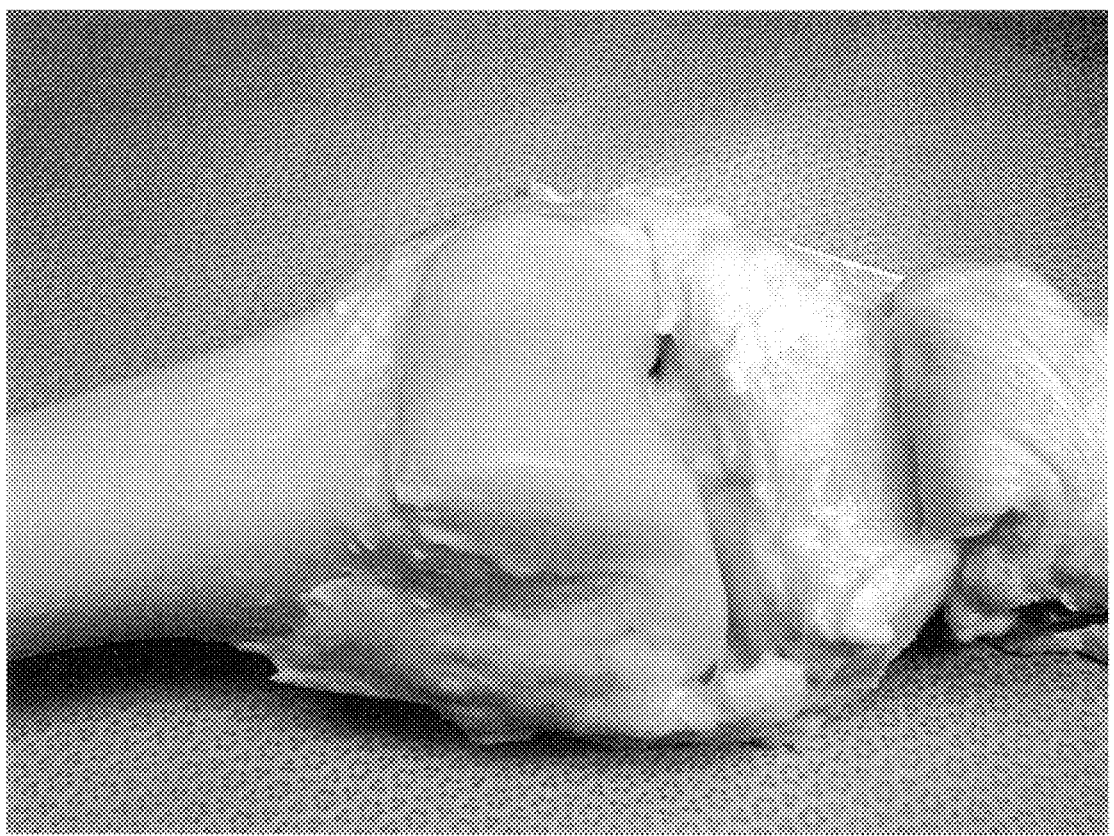
FIG. 7 is a photograph of an intact knee, including proximal tibia, distal femur and patella, along with articulating tendons and ligaments, before treatment according to the method of this invention.

FIG. 7 is a photograph of an intact knee, including proximal tibia, distal femur and patella, along with articulating tendons and ligaments, before treatment according to the method of this invention.

Figure 8:
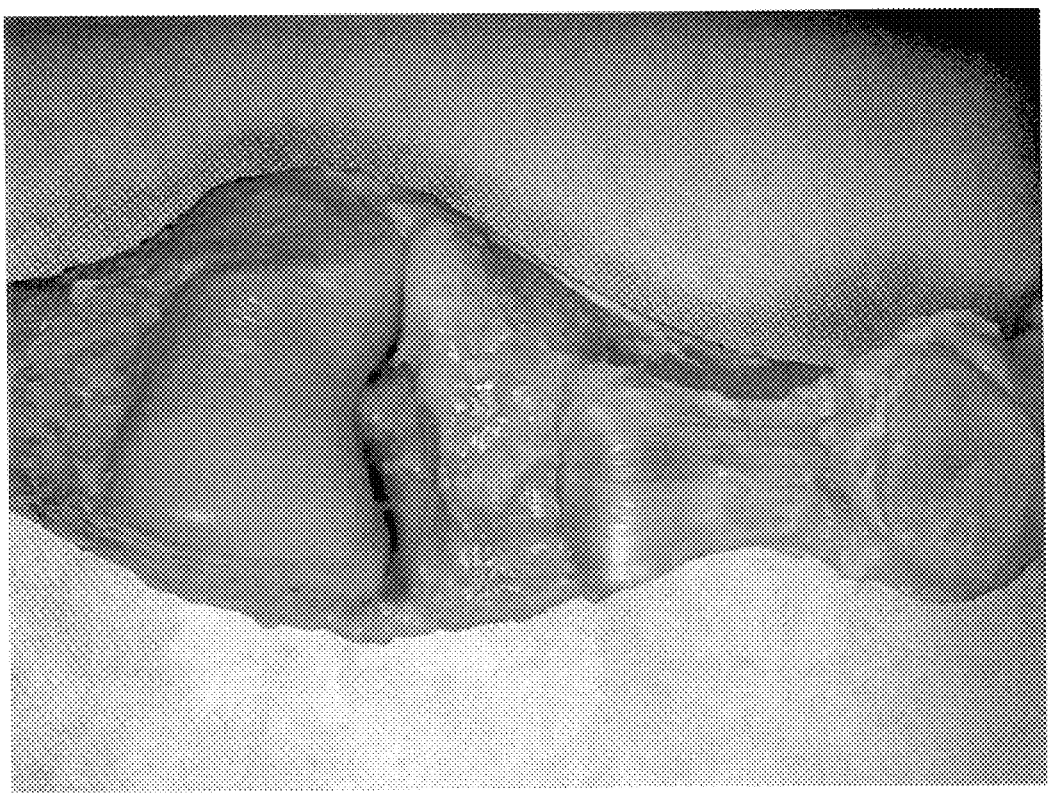
FIG. 8 is a photograph of the intact knee shown in FIG. 7, after treatment according to the method of this invention, showing cleanliness of the implant, and preservation of the articulating tendons and ligaments.

FIG. 8 is a photograph of the intact knee shown in FIG. 7, after treatment according to the method of this invention, showing cleanliness of the implant, and preservation of the articulating tendons and ligaments.

In light of these results, it will be apparent that implant materials and tissues that may be effectively cleaned according to this procedure include, but are not limited to metallic implants, synthetic implants, ceramic implants, allograft, autograft or xenograft tissues. Such tissues may be selected from tissues comprising: cortical bone, cancellous bone, fascia, whole joints, tendons, ligaments, dura, pericardia, heart valves, veins, neural tissue, submucoal tissue, (e.g. intestinal tissue), and cartilage. Essentially any implantable material having an internal matrix that is required to be cleaned may be treated to advantage according to the method of this invention.

Example 4

Effectiveness of the Process of this Invention for Deep Cleaning of Implants

Figure 9:
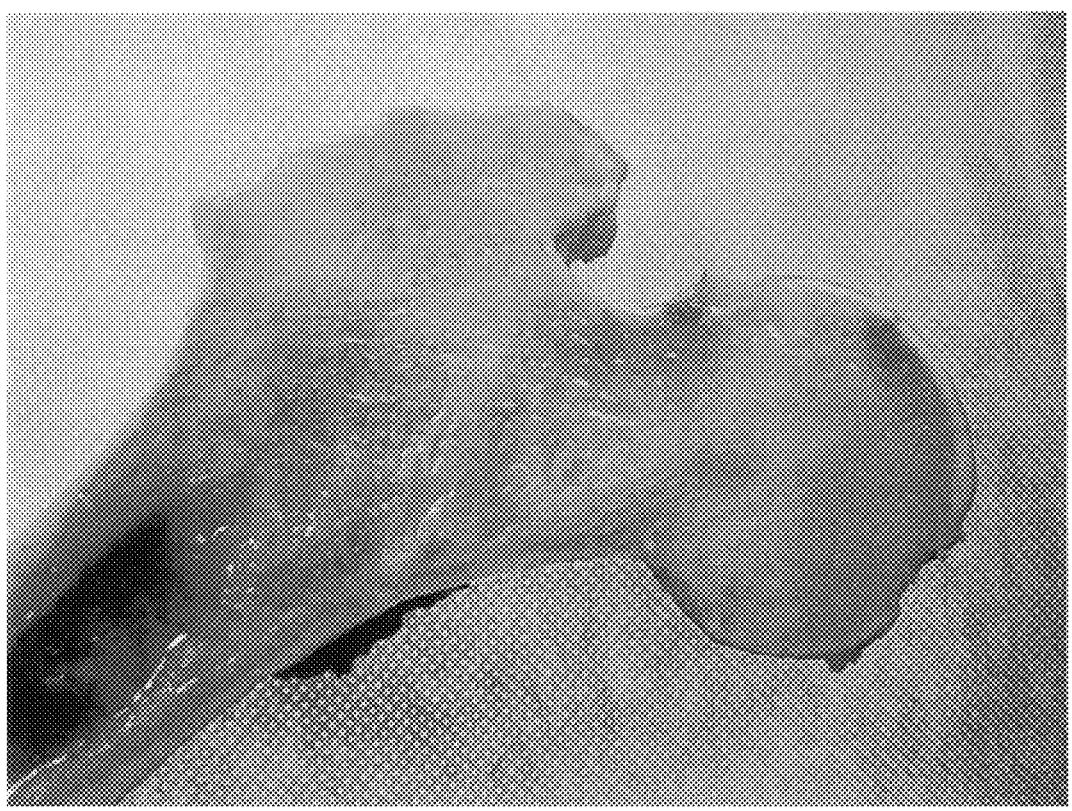
FIG. 9 is a photograph of an anterior aspect of a coronal section through the proximal femur prior to treatment according to the method of this invention.

FIG. 9 is a photograph of an anterior aspect of a coronal section through the proximal femur prior to treatment according to the method of this invention.

Figure 10:
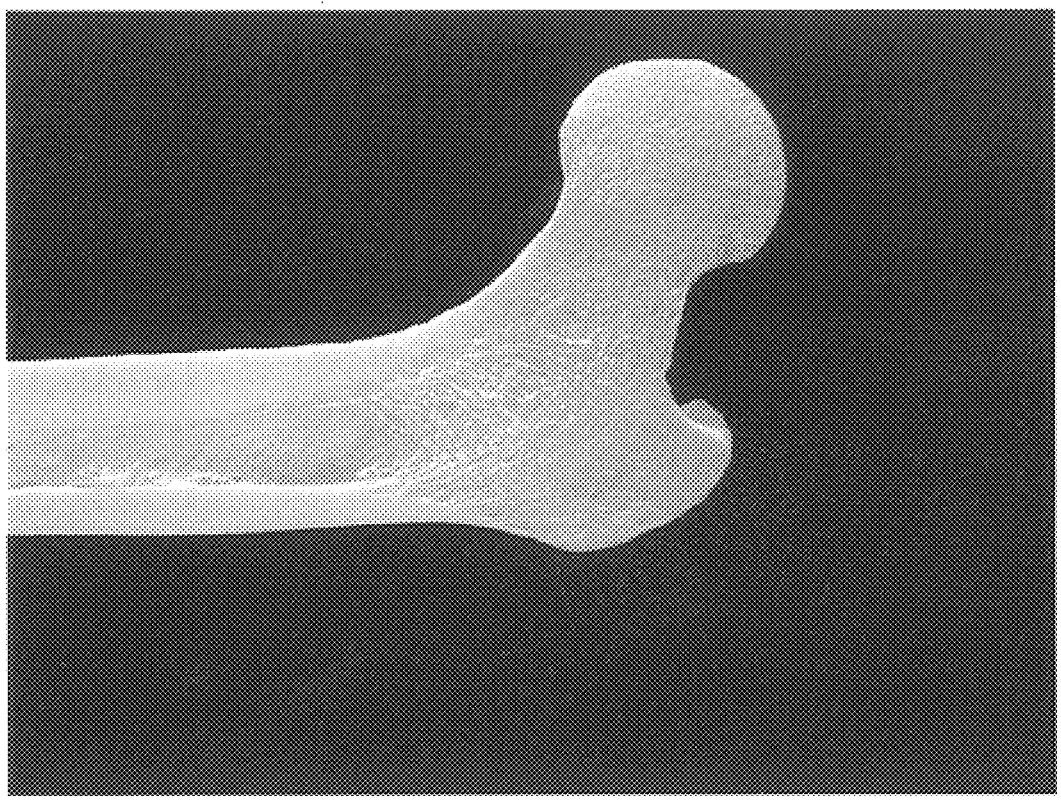
FIG. 10 is a photograph of the posterior aspect of the coronal section through the proximal femur shown in FIG. 9, after treatment according to the method of this invention.

FIG. 10 is a photograph of the posterior aspect of the coronal section through the proximal femur shown in FIG. 9, after treatment according to the method of this invention.

Figure 11:
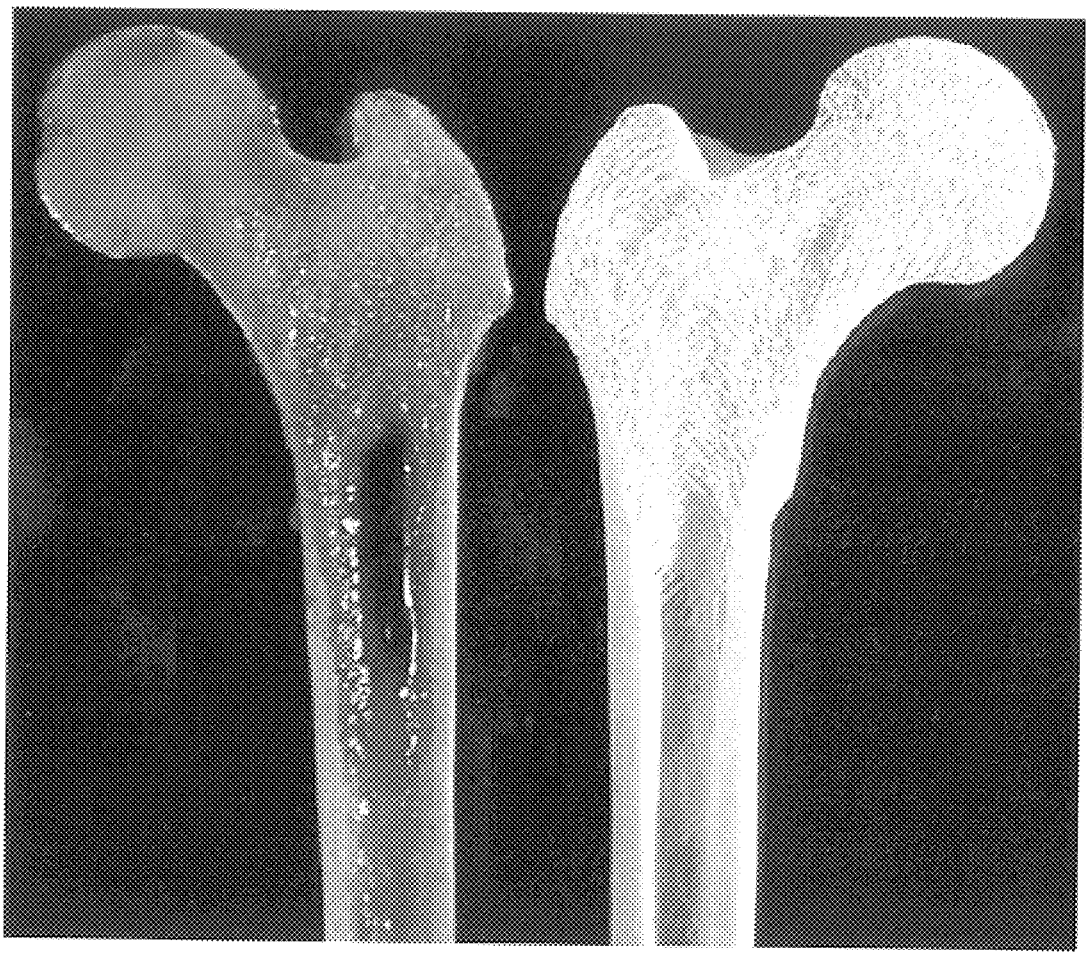
FIG. 11 is a photograph of the sections shown in FIGS. 9 and 10, side-by-side, demonstrating the effectiveness of the treatment according to this invention for removal of endogenous substances.

FIG. 11 is a photograph of the sections shown in FIGS. 9 and 10, side-by-side, demonstrating the effectiveness of the treatment according to this invention for removal of endogenous substances and deep, penetrating implant cleaning.

Example 5

Figure 12:
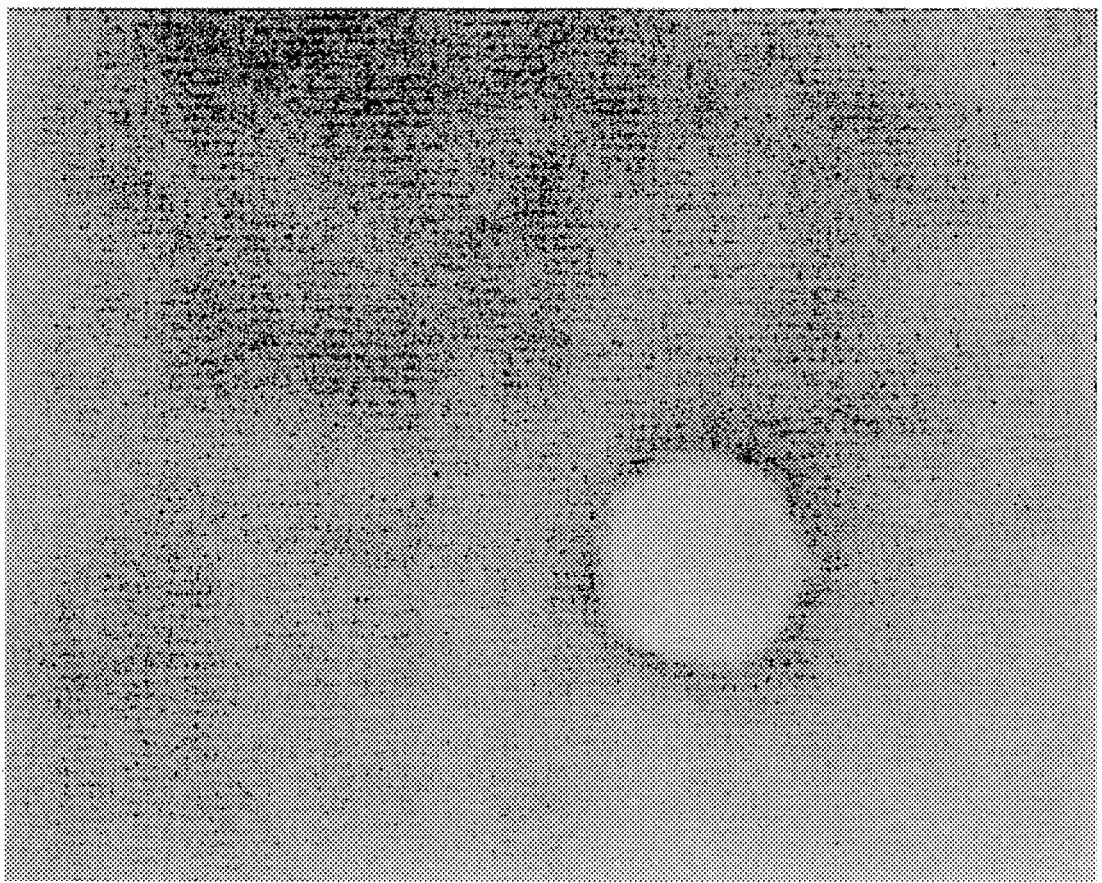
FIG. 12 is a photomicrograph of an osteon from cortical bone without fluoroisothiocyanate (FITC) fluorescent dye treatment (400×magnification).

Demonstration of the Ability of the Process of this Invention to Achieve Deep Interpenetration of Cleaning Substances and Impregnation of Implants with Desirable Biologically Active Substances FIG. 12 is a photomicrograph of an osteon from cortical bone without fluoroisothiocyanate (FITC) fluorescent dye treatment (100×magnification).

Figure 13:
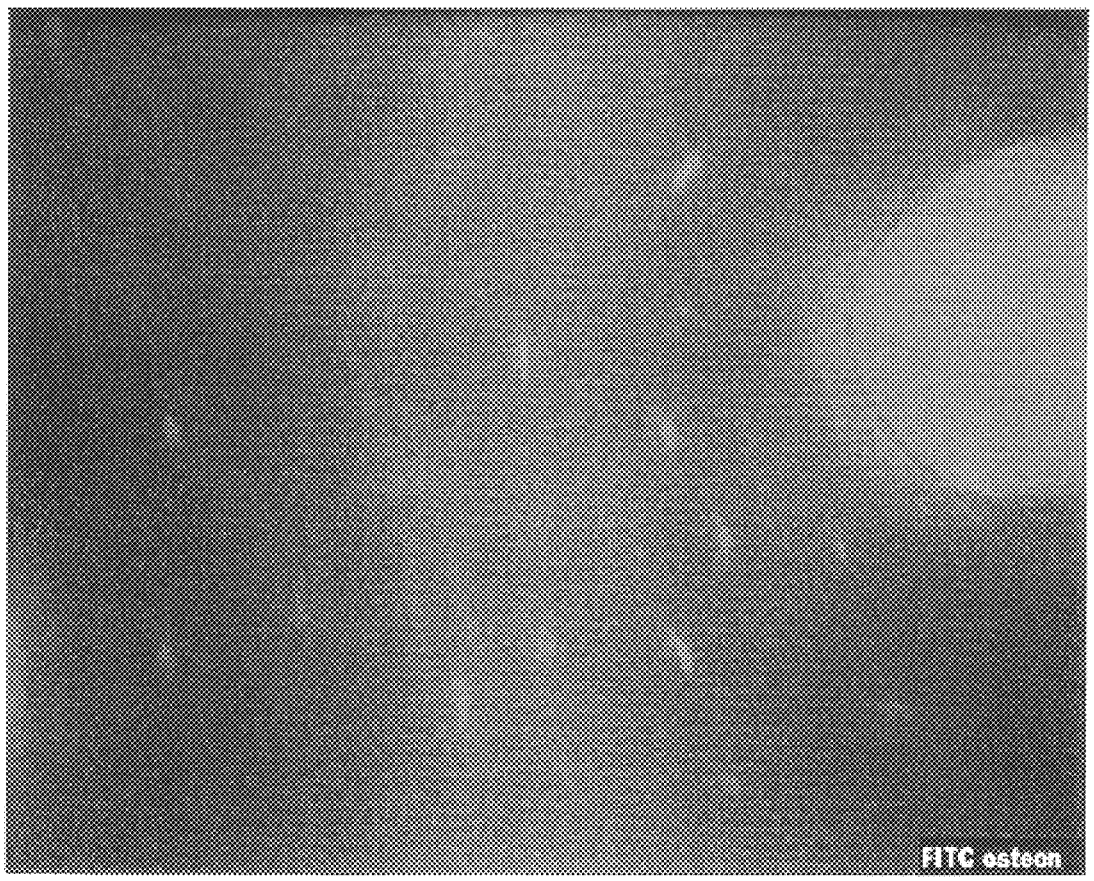
FIG. 13 is a photomicrograph of an osteon from cortical bone after inclusion of FITC in one of the cleaning solutions of this invention, demonstrating deep interpenetration of the dye into the smallest of bone interstices—bright green areas indicating structures containing FITC, including the large haversian canal (right margin) and smaller satellite lacunae (central area; 400×magnification).

FIG. 13 is a photomicrograph of an osteon from cortical bone after inclusion of FITC in one of the cleaning solutions of this invention, demonstrating deep interpenetration of the dye into the smallest of bone interstices—bright green areas indicating structures containing FITC, including the large haversian canal (right margin) and smaller satellite lacunae (central area; 100×magnification).

These photomicrographs demonstrate that the FITC dye is forced into the smallest implant interstices, thereby revealing the ability to achieve deep penetrating cleaning. In addition, these photomicrographs demonstrate that biologically active substances, such as antibiotics, antiviral compounds, anti-inflammatory compounds, growth factors, osteo-inductive substances (e.g. bone morphogenetic protein, cartilage derived morphogenetic protein, natural or recombinant, and the like), when included in solutions employed according to the method of this invention, may be effectively imbedded deeply into implant materials. Thus, biologically active substances for permeation into implants, according to the method of this invention are selected from the group consisting of bone morphogenetic protein, tissue growth factor beta or member of the tissue growth factor beta family of growth factors, cartilage derived morphogenetic proteins I or II or both, and any related cartilage derived growth factors, angiogenic factors, platelet derived growth factor. Any of the proteins selected for permeation into implants may be natural or recombinant proteins.

What is claimed is:

1. An implant cleaning, perfusion and passivation process which comprises subjecting the entire implant to cyclic exposure of increased and decreased pressure above one atmosphere or below one atmosphere or both, wherein said implant consists essentially of autograft, allograft or xenograft tissue, or combinations thereof; said process comprising
   a. evacuating a chamber containing said implant to a pressure that is sufficiently decreased such that internal channels present in the implant are primed for backfilling with cleaning solutions;
   b. backfilling said implant with a cleaning solution or a mixture of cleaning solutions;
   c. pressurizing said chamber; and
   d. cycling between steps (a) and (c) for between about 1–150 cycles, maintaining a temperature of between about 35–40 degrees centigrade, with optional application of ultrasonic energy.

2. The process according to claim 1 wherein said cyclic exposure of said implant to increased and decreased pressures occurs in the presence of a cleaning solution.

3. The process according to claim 2 wherein said process occurs, at least in part, with concurrent exposure of said implant to sonication.

4. The process according to claim 3 wherein said cycling between increased and decreased pressures occurs according to a defined program.

5. The process according to claim 4 wherein said implant is cortical bone, cancellous bone, fascia, whole joints, tendons, ligaments, dura, pericardia, heart valves, veins, neural tissue, submucosal tissue or cartilage, or combinations thereof.

6. The process according to claim 5 wherein said cycling of increased and decreased pressures is achieved through an oscillation of pressure in a chamber containing said implant in the presence of a cleaning solution.

7. The process according to claim 1, further comprising:
   e. machining said implant to final dimensions if not previously so machined.

8. The process according to claim 7, further comprising the step of:
   f. conducting steps (a)–(d) using the same or a different cleaning solutions.

9. The process according to claim 8, wherein step (f) is conducted under elevated or reduced temperatures, with respect to ambient temperature.

10. The process according to claim 9, further comprising placing said implant into a sterile, sealable package, and performing a surface decontamination step prior to or after sealing said package.

11. The process according to claim 1 wherein said implant is tissue derived from a single donor.

12. The process according to claim 1 wherein said implant is tissue derived from a pool of donor tissues.

13. The process according to claim 1 wherein said cleaning solution is selected from the group consisting of sterile water, Triton X-100, TNBP, 3% hydrogen peroxide, a water miscible alcohol, saline solution, providone iodine, ascorbic acid solution, aromatic hydrocarbons, aliphatic hydrocarbons, ethers, ketone, amines, urea, guanidine hydrochloride, esters, glycoproteins. proteins, saccharides, enzymes, gasseous acids, gasseous peroxides, and mixtures thereof.

14. The process according to claim 11 wherein said tissue is pooled with similarly treated tissue from at least one other donor, and is further cleaned by conducting steps (a)–(d) using the same or different cleaning solutions.

15. The process according to claim 14 wherein said cleaning solution is selected from the group consisting of 6% hydrogen peroxide, 1% sodium hypochlorite, 6M urea, 4M guanidine hydrochloride, 1 N sodium hydroxide, isopropanol, water, saline and mixtures thereof.

16. The process according to claim 15 wherein said process is conducted at a temperature between about thirty seven degrees centigrade and about eighty degrees centigrade.

17. The process according to claim 16 wherein said process is conducted at about 50–60 degrees centigrade.

18. The process according to claim 12 wherein said tissue is pooled with similarly treated tissue from at least one other donor, and is cleaned by conducting steps (a)–(d) using the same or different cleaning solutions.

19. The process according to claim 18 wherein said cleaning solution is selected from the group consisting of 6% hydrogen peroxide, 1% sodium hypochlorite, 6M urea, 4 M guanidine hydrochloride, 1 N sodium hydroxide, isopropanol, water, saline and mixtures thereof.

20. The Process according to claim 19 wherein said process is conducted at a temperature between about thirty-seven degrees centigrade and about eighty degrees centigrade.

21. The process according to claim 20 wherein said process is conducted at about 50–60 degrees centigrade.

22. The process according to claim 1 wherein the thus treated implant is packaged in a sterile environment upon performing a surface or terminal decontamination step.

23. The process according to claim 22 wherein said surface or terminal decontamination step comprises contacting the implant with vapor-phase $H_2O_2$, peracetic acid, exposure to gamma irradiation, electron beam irradiation, exposure to ethylene oxide, or a mixture of these.

24. The process according to claim 22, wherein said implant is in its final packaging.

25. The process according to claim 1 wherein the implant is perfused or coated with a bioactive substance.

26. The process according to claim 25 wherein said bioactive substance is a drug or a growth factor.

27. The process according to claim 26 wherein said growth factor is selected from the group consisting of a bone morphogenetic protein, tissue growth factor beta or member of the tissue growth factor beta family of growth factors, cartilage derived morphogenetic proteins I or II or both, and any related cartilage derived growth factors, angiogenic factors, and platelet derived growth factor.

28. The process according to claim 1 which results in any one or all of:

between about a one to twelve log reduction in bacterial contamination;

(a) between about a one to fifteen log reduction in enveloped virus contamination;

(b) up to about a five log reduction in non-enveloped virus contamination;

(c) between about a two to ten fold reduction in endotoxin;

(d) maintenance of implant or graft biologic and biomechanical properties;

(e) absence of tissue toxicity due to cleaning solutions used;

(f) reduced implant antigenicity.

29. An implant cleaning, perfusion and passivation process which comprises subjecting the entire implant to cyclic exposure of increased and decreased pressure above one atmosphere or below one atmosphere or both, wherein said implant consists essentially of autograft, allograft or xenograft tissue, or combinations thereof; and wherein cycling of pressures is conducted between pressures below one atmosphere of between about 60 to 100 torr, and pressures above one atmosphere are utilized to backfill said implant with solutions in contact with the implant at pressures between about 6–10 atmospheres, wherein concurrent sonication occurs throughout or at specific stages in said cycling of pressures.

30. An implant cleaning, perfusion and passivation process which comprises subjecting said implant to cyclic exposure of increased and decreased pressures above one atmosphere or below one atmosphere or both; wherein said cyclic exposure is achieved through an oscillation of pressure in a chamber containing said implant; the process comprising the steps of:

(a) evacuating said chamber containing said implant;

(b) backfilling said implant with a cleaning solution or a mixture of cleaning solutions;

(c) pressurizing said chamber; and (c) cycling between steps (a) and (c) more than 2 cycles; and wherein sonication occurs throughout or at specific stages in said cycling of pressures; and wherein said implant consists essentially of autograft allograft or xenograft tissue, or combinations thereof.

31. The process according to claim 30, wherein pressures below one atmosphere down to 60 torr and pressures above one atmosphere up to 10 atmospheres are employed.

32. The process according to 31, wherein pressures below one atmosphere are between about 60 to 100 torr and pressures above one atmosphere are between about 6 to 10 atmospheres.

* * * * *